US008346348B2

(12) United States Patent
Onimura

(10) Patent No.: US 8,346,348 B2
(45) Date of Patent: Jan. 1, 2013

(54) OPTICAL COHERENT CROSS-SECTIONAL IMAGE FORMING APPARATUS AND CONTROL METHOD FOR CONTROLLING SUCH APPARATUS

(75) Inventor: Yuuji Onimura, Fujinomiya (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 18 days.

(21) Appl. No.: 13/072,148

(22) Filed: Mar. 25, 2011

(65) Prior Publication Data
US 2011/0237958 A1 Sep. 29, 2011

(30) Foreign Application Priority Data
Mar. 26, 2010 (JP) ................................. 2010-073402

(51) Int. Cl.
*A61B 6/00* (2006.01)
(52) U.S. Cl. ........................................ 600/478; 600/477
(58) Field of Classification Search ........... 600/473–480
See application file for complete search history.

(56) References Cited

U.S. PATENT DOCUMENTS

| 6,134,003 | A | 10/2000 | Tearney et al. | |
|---|---|---|---|---|
| 6,994,667 | B2* | 2/2006 | Singh | 600/105 |
| 7,491,165 | B2* | 2/2009 | Kogasaka et al. | 600/104 |
| 7,850,642 | B2* | 12/2010 | Moll et al. | 604/95.04 |
| 7,963,288 | B2* | 6/2011 | Rosenberg et al. | 128/898 |
| 8,016,753 | B2* | 9/2011 | Sugita | 600/156 |
| 8,167,808 | B2* | 5/2012 | Sato | 600/459 |
| 2004/0082939 | A1* | 4/2004 | Berlin | 606/5 |
| 2006/0281973 | A1* | 12/2006 | Sugita | 600/156 |
| 2007/0232893 | A1* | 10/2007 | Tanioka | 600/407 |
| 2008/0243162 | A1* | 10/2008 | Shibata et al. | 606/185 |
| 2009/0122320 | A1 | 5/2009 | Petersen et al. | |
| 2009/0143686 | A1 | 6/2009 | Onimura et al. | |
| 2009/0247878 | A1* | 10/2009 | Tanioka et al. | 600/462 |
| 2011/0245610 | A1* | 10/2011 | Tanaka | 600/114 |
| 2011/0245683 | A1* | 10/2011 | Onimura | 600/476 |
| 2012/0004668 | A1* | 1/2012 | Wallace et al. | 606/130 |

FOREIGN PATENT DOCUMENTS

| JP | 2009-128074 A | 6/2009 |
|---|---|---|
| WO | 2006/024015 A1 | 3/2006 |

OTHER PUBLICATIONS

European Search Report issued Jul. 28, 2011 by the European Patent Office in corresponding European Application No. 11 159 803.3.

* cited by examiner

*Primary Examiner* — Sanjay Cattungal
(74) *Attorney, Agent, or Firm* — Buchanan Ingersoll & Rooney PC

(57) ABSTRACT

An optical coherent cross-sectional image forming apparatus in which light outputted from a light source is divided into a measurement light and a reference light inside the apparatus and in which a cross-sectional image is formed based on a coherent light, produced from a reflected light obtained by emitting the measurement light to a biological tissue through a probe inserted into a body lumen, and the reference light, wherein the apparatus includes a detector for detecting that a transmitting and receiving unit entered inside a guiding catheter for guiding the probe by using data during the axial-direction movement and a controller for stopping at least a portion of a process associated with from generation to holding of the cross-sectional image based on the optical coherence in a case in which it is detected by the detector that the transmitting and receiving unit entered inside the guiding catheter.

15 Claims, 12 Drawing Sheets

OPTICAL COHERENT CROSS-SECTIONAL IMAGE FORMING APPARATUS AND CONTROL METHOD FOR CONTROLLING SUCH APPARATUS

This application contains subject matter disclosed in, and claims priority to, Japanese Patent Application No. 2010-073402 filed in the Japanese Patent Office on Mar. 26, 2010, the entire content of which is incorporated herein by reference.

TECHNICAL FIELD

The present invention generally pertains to an optical coherent cross-sectional image forming apparatus and a control method for controlling such an apparatus.

BACKGROUND DISCUSSION

In the past, there has been used an optical coherent tomography apparatus (Optical Coherent Tomography: OCT) for diagnosing arteriosclerosis, for diagnosis before operation at the time of treatment inside a blood vessel depending on a high functional catheter such as a balloon catheter, a stent and the like or for a result confirmation after an operation. In an optical coherent tomography apparatus, radial scan is carried out by inserting a catheter installed with an optical fiber which is attached with an optical lens and an optical mirror at the distal end thereof into a blood vessel, by illuminating light into a blood vessel while rotating the optical mirror and by receiving reflected light from a biological tissue. Then, in the optical coherent tomography apparatus, a cross-sectional image of a blood vessel is drawn-out (prepared) based on the reflected light obtained by this radial scan. Further, as an improvement of the optical coherent tomography apparatus, there has been developed an optical frequency domain imaging apparatus utilizing a wavelength sweep (see, for example, Japanese unexamined patent publication No. 2009-128074).

The optical coherent tomography apparatus, inside the apparatus, divides a light outputted from a light source into a measurement light and a reference light, and emits the measurement light from a distal end thereof through an optical fiber inside a catheter. Then, by taking-in a reflected light reflected from a biological tissue inside the apparatus through the same optical fiber, and by making the reflected light and the reference light interfere each other, it is possible to obtain intensity of the measurement light from the same optical path length as that of the reference light, more specifically, to obtain intensity of the reflected light.

In the optical coherent tomography apparatus as mentioned above, a reflected light is obtained by reflecting the reference light on the mirror inside the apparatus and concurrently, the optical path length of the reference light is scanned by moving the mirror position forward and backward. Then, owing to a fact that a coherent light between the reference light and the reflected light is obtained in synchronization with the scanning of this optical path length, it is possible to obtain reflection-intensity distribution in the depth direction. In an optical coherent tomography apparatus, a radial scan is carried out by rotating the optical fiber axially and a blood vessel cross-sectional image is drawn out.

On the other hand, there has been proposed an optical frequency domain imaging apparatus in which a cross-sectional image is formed by utilizing a wavelength sweep instead of changing the optical path length of the reference light. In an optical frequency domain imaging apparatus using the wavelength sweep, there is obtained a reflection-intensity distribution of the depth direction with reference to a point, at which the optical path difference between the measurement light and the reference light is same, from the frequency distribution of the obtained coherent light by sweeping the wavelength of the emitted light repeatedly without scanning the optical path length of the reference light.

In an ultrasonic diagnosis apparatus, a pull-back operation (operation of axially moving an ultrasonic transducer) is carried out at a speed around 1 mm/sec, so that it was possible for an operator to set an area to be observed while confirming the picture screen. On the other hand, in an optical coherence diagnosis apparatus, data are obtained speedily during the period of removing blood depending on flash liquid, so that usually there is employed a system in which a distance as long as possible is recorded at once and a slow reproduction is carried out later on. At that time, the position for recording the image is confirmed while observing a CAG or OFDI image, but there was no other way than a way in which the record termination is carried out by a manual termination operation or by thoroughly pulling all the distance which can be pulled-back.

Usually, a guiding catheter is used for guiding a probe which contains a catheter sheath and an imaging core until a cross-section imaging position is reached inside a blood vessel. For example, a guiding catheter is passed-through until reaching a vicinity of the imaging position of a coronary artery by way of a femoral artery and the probe is guided to the imaging position by using a guide wire. Therefore, at the time of such a procedure, for example, as shown in FIG. 6, it happens that a scan will be carried out by protruding a probe which includes a catheter sheath (301) and an imaging core (601, 602, 231) from a guiding catheter. For that reason, a transmitting and receiving unit for transmitting a measurement light and receiving a reflected light on the way of pull-back scan enters the inside of the guiding catheter. When the transmitting and receiving unit enters the inside of the guiding catheter, the measurement light to the portion desired to be observed or the reflected light from the portion desired to be observed will be blocked and significant data cannot be obtained even if the recording is continued. However, as a result of analyzing the data obtained at a facility in cooperation with a well trained technical expert, a guiding catheter was recorded for the length of 30% to 60% of the obtained data and these data are thoroughly unnecessary data. The problem caused by recording unnecessary data in this manner will be described hereinafter.

When recording an image, some sort of flash liquid is injected by an injector, a contrast syringe or the like in order to remove blood. For example, when selecting a contrast agent as the flash liquid, usually, it happens that a quantity of around 10 ml to 20 ml is to be injected per one pull-back scan, and several 10% thereof are the quantity which is injected after the probe enters the guiding catheter. There is possibility that the injection of such a flash liquid may exert influence on a renal function or another physiological function of a patient and it is thus preferable to limit the injection of the flash liquid to a requisite minimum value.

In addition, by recording a useless image, the data volume will increase by an amount of around a few 10 percent to a hundred percent, it is needless to say that the time period required for the data handling also increases, and the time period which can be used for the diagnosis under normal circumstances will be compressed. Further, the space necessary for storing inspection data will also increase by a similar ratio.

SUMMARY

The apparatus and method disclosed here reduces unnecessary information recording and reduces the unnecessary injection of flash liquid.

In the optical coherent cross-sectional image forming apparatus disclosed here, light outputted from a light source is divided into a measurement light and a reference light inside the apparatus and in which a cross-sectional image is formed based on a coherent light, which is obtained from a reflected light obtained by emitting the measurement light to a biological tissue through a probe inserted into a body lumen, and the reference light. The apparatus includes: a transmitting and receiving unit at a distal end portion of the probe, wherein the transmitting and receiving unit emits the measurement light and also receives the reflected light, with the transmitting and receiving unit being axially movable relative to a catheter sheath during operation of the apparatus; a scanning drive unit connected to the transmitting and receiving unit to rotate and axially move the transmitting and receiving unit; generating and holding means for generating data, corresponding to the cross-sectional image, using the coherent light between the reflected light obtained through the transmitting and receiving unit and the reference light, and for holding the data; means for detecting, through use of the data held by the generating and holding means, that the transmitting and receiving unit has entered inside the catheter sheath during the axial movement; and a controller for stopping at least a portion of an operational aspect of the apparatus, from when the data corresponding to the cross-sectional image is generated to when the data is held, whenever the means for detecting detects that the transmitting and receiving unit has entered the catheter sheath.

In addition, another aspect involves a method for controlling an optical coherent cross-sectional image forming apparatus in which light outputted from a light source is divided into a measurement light and a reference light inside the apparatus and in which a cross-sectional image is formed based on a coherent light obtained from reflected light, acquired when the measurement light emitted toward a biological tissue through a probe inserted into a body lumen is reflected, and the reference light. The method involves rotating and axially moving a transmitting and receiving unit at a distal end portion of the probe which emits the measurement light and receives the reflected light, the transmitting and receiving unit being axially moved relative to a guiding catheter; generating data corresponding to the cross-sectional image using the coherent light and holding the data in a memory unit; determining when the transmitting and receiving unit has entered inside the guiding catheter during the axial movement of the transmitting and receiving unit; and stopping at least a portion of an operational aspect of the apparatus occurring between the generation of the data and the holding of the data whenever it is determined that the transmitting and receiving unit has entered inside the guiding catheter.

The optical coherent tomography apparatus is able to repress unnecessary image recording. There can also be realized: a reduction of flash liquid such as a contrast agent, a physiological salt solution and the like; compression of recording data amount; reduction of steering time; reduction of back-up time; and reduction of image confirmation time period.

DETAILED DESCRIPTION

Hereinafter, examples of several embodiments of the apparatus and method will be explained in detail with reference to the accompanying drawing figures.

First Embodiment

A first example of an embodiment of the apparatus and method disclosed here is an optical coherent tomography apparatus (OCT apparatus) inside a body lumen in which an optical path length of reference light is scanned and reflection-intensity distribution in the depth direction is obtained.

1. Overall Construction of Imaging Diagnostic Apparatus

Figure 1:
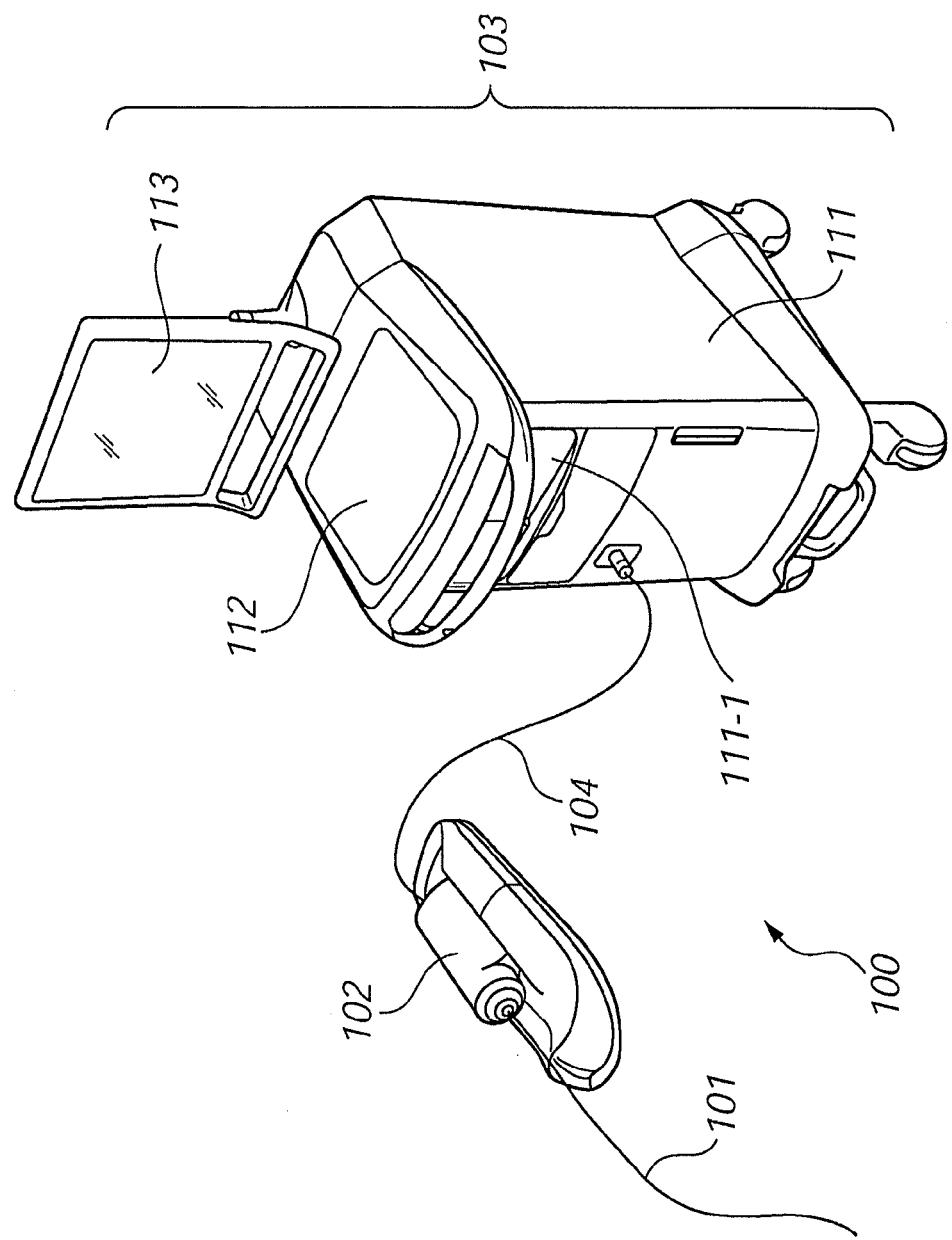
FIG. 1 is a perspective view of an example of an imaging diagnostic apparatus disclosed here.

Referring to FIG. 1, the imaging diagnostic apparatus 100 (optical coherent tomography apparatus) according to a first embodiment disclosed by way of example is an optical coherent cross-sectional image forming apparatus provided with an optical probe unit 101, a scanner & pull-back unit 102 and a steering control apparatus 103, and the scanner & pull-back unit 102 and the steering control apparatus 103 are connected by a signal line & optical fiber 104.

The optical probe unit 101 is directly inserted inside a body lumen of a blood vessel or the like and measures a state of a biological tissue by using an imaging core which will be described later. The scanner & pull-back unit 102 is constructed so as to be detachable with respect to the optical probe unit 101 and defines a radial operation of the imaging core inside the optical probe unit 101 according to the driving operation of an installed motor.

The steering control apparatus 103 is configured to permit, when carrying out the optical coherence imaging diagnosis inside the body lumen, the inputting of various kinds of setting values, and process data obtained by the measurement to display data as a cross-sectional image. The steering control apparatus 103 includes a main body control unit 111 so that the data obtained by the measurement is processed and the processed result is outputted. Also included is a printer & DVD recorder 111-1 so that the processed result in the main body control unit 111 is printed and is stored as data signals.

An operation panel 112 allows a user to carry out inputs of various kinds of setting values and instruction. An LCD monitor 113 is a display apparatus (display) which displays the processed result in the main body control unit 111.

2. Operational Aspects of Optical Coherent Tomography Apparatus

Figure 2:
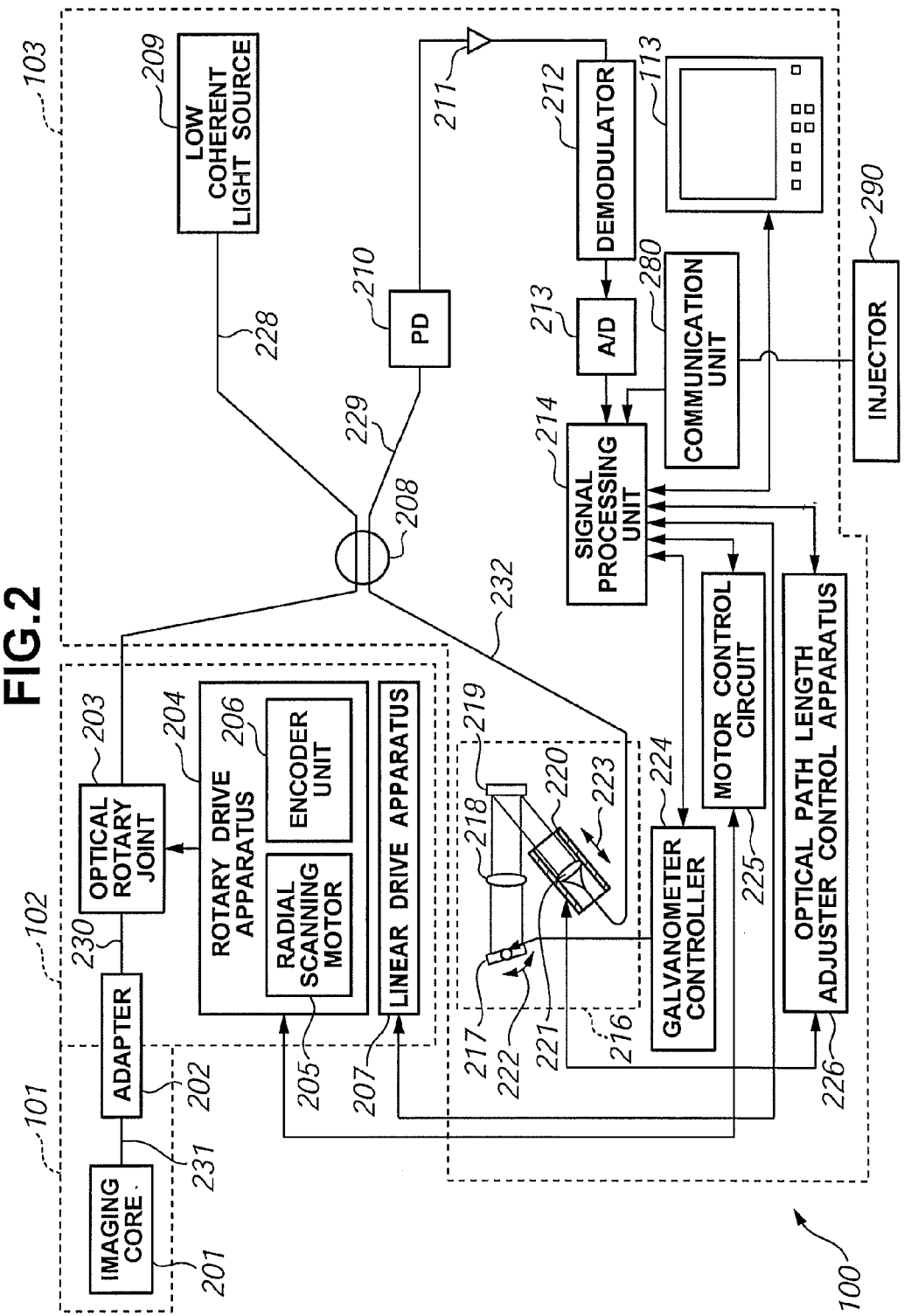
FIG. 2 is a block diagram of the example of the imaging diagnostic apparatus shown in FIG. 1.

Referring to FIG. 2, set forth below is a discussion of main functional or operational aspects of the optical coherent tomography apparatus within the optical imaging diagnostic apparatus 100 according to this embodiment disclosed by way of example.

In FIG. 2, a reference numeral 209 indicates a low coherent light source of a super high intensity light-emitting diode or the like. The low coherent light source 209 outputs a low coherent light whose wavelength is around 1310 nm and which shows coherence only in such a short distance range in which a coherent-able distance thereof (coherent length) is around a few μm to ten and a few μm. Consequently, in a case in which this light is divided into two light paths and thereafter, the light paths are mixed again, the light is to be detected as a coherent light in a case in which the difference between the two optical path lengths from a point at which the light is divided to a point at which they are mixed is within a short distance range of around a few μm to ten and a few μm, and the light is never detected as a coherent light in a case in which the difference of the optical path lengths is larger than that. The coherent light is thus obtained from the reflected light and the reference light.

The light of the low coherent light source 209 enters one end of a first single mode fiber 228 and is transmitted to the distal end surface side of the fiber. The first single mode fiber 228 is connected optically with a second single mode fiber 229 and a third single mode fiber 232 by a photo coupler unit 208 on the way. The photo coupler unit is an optical component in which it is possible to divide one optical signal into two or more outputs and/or to combine two or more inputted optical signals into one output and the light of the low coherent light source 209 can be transmitted by being divided into three optical paths at the maximum by the photo coupler unit 208.

The scanner & pull-back unit 102 is provided on the distal end side ahead of the photo coupler unit 208 of the first single mode fiber 228. In the inside of a rotary drive apparatus 204 of the scanner & pull-back unit 102, there is provided an optical rotary joint (optical coupling portion) 203 for connecting between a non-rotary portion (fixed portion) and a rotary portion (rotary drive portion) and for transmitting the light. Further, the distal end side of a fourth single mode fiber 230 in the inside of the optical rotary joint 203 is connected freely detachably with a fifth single mode fiber 231 of the optical probe unit 101 through an adapter 202. Thus, the light from the low coherent light source 209 is transmitted to the fifth single mode fiber 231 which is passed-through in the imaging core 201 which repeats the transmitting and receiving of the light and which is rotary-drivable.

The light transmitted to the fifth single mode fiber 231 is illuminated or transmitted while radially operating with respect to the biological tissue inside the blood vessel from the distal end side of the imaging core 201. Then, a portion of the reflected light scattered on the surface or on the inside of the biological tissue is received or taken-in by the imaging core 201 and returns to the first single mode fiber 228 side through a reverse optical path, and a portion thereof moves to the second single mode fiber 229 side by the photo coupler unit 208. In the second single mode fiber 229, the reflected light is mixed with a reference light mentioned later and it is emitted from one end of the second single mode fiber 229 as the coherent light and is light-received by a photo detector 210 (for example, photo diode).

The rotary drive portion side of the optical rotary joint 203 is rotatingly driven by a radial scanning motor 205 of the rotary drive apparatus 204. Also, a rotary angle of the radial scanning motor 205 is detected by an encoder unit 206. Further, the scanner & pull-back unit 102 is provided with a linear drive apparatus 207 and movement (axial-direction operation) in an axial direction (distal direction inside the body lumen and opposite direction thereof) of the imaging core 201 is defined based on an instruction from a signal processing unit 214. The axial-direction operation is realized owing to a fact that the linear drive apparatus 207 makes the scanner including the optical rotary joint 203 move based on a control signal from the signal processing unit 214.

At that time, owing to a fact that only the imaging core 201 stored in a catheter sheath moves axially while the catheter sheath of the optical probe unit 101 (mentioned later by FIG. 3 and FIG. 5) is maintained to be fixed in the blood vessel, the axial-direction operation is carried out without injuring a blood vessel wall.

A variable mechanism 216 of the optical path length for changing the optical path length of the reference light is provided on the opposite side with respect to the photo coupler unit 208 of the third single mode fiber 232 (on the reference light path). The variable mechanism 216 of this optical path length is provided with a first optical path length changing unit for readily speedily changing the optical path length which corresponds to an inspection region in the depth direction (direction of emission of the measurement light) of the biological tissue and a second optical path length changing unit for changing the optical path length which corresponds to fluctuation of the length thereof to absorb the fluctuation of the length of the individual optical probe unit 101 in case the optical probe unit 101 is exchanged.

Facing the distal end of the third single mode fiber 232, there is arranged, through a collimating lens 221 which is freely movable in the direction shown by the arrow 223, a mirror 219 which is mounted on an one-axis stage 220 together with this distal end. Also, there is mounted, through a mirror 218 corresponding to this mirror 219 (diffraction lattice), with a galvanometer 217 which is rotatable by a fine angle as the first optical path length changing unit. This galvanometer 217 is rotated relatively speedily in the direction of the arrow 222 by a galvanometer controller 224.

The galvanometer 217 is a device which reflects light by a mirror of the galvanometer and it is configured such that the mirror mounted on a movable portion thereof is to be rotated quite speedily by applying an AC drive signal to the galvanometer which functions as a reference mirror. That is to say, owing to a fact that the drive signal is applied with respect to the galvanometer 217 from the galvanometer controller 224 and it is rotated rather speedily by the drive signal in the direction of the arrow 222, the optical path length of the reference light changes fairly speedily only by the optical path length which corresponds to the inspection region in the depth direction of the biological tissue. One cycle of the change of this optical path difference becomes a cycle of obtaining coherent light for one line.

On the other hand, the one-axis stage 220 functions as the second optical path length changing unit having such an amount of variable range of optical path length, which can absorb the fluctuation of the optical path length of the optical probe unit 101 in case of exchanging the optical probe unit 101. Further, the one-axis stage 220 operates as an adjuster for adjusting an offset. For example, even in a case in which the distal end of the optical probe unit 101 is not closelyattached to the surface of the biological tissue, it is possible, by changing the optical path length by the one-axis stage 220, to set it in a state of interfering with the reflected light from the surface position of the biological tissue.

The light whose optical path length is changed by the variable mechanism 216 of the optical path length is mixed with the light (reflected light) obtained from the first single mode fiber 228 side by the photo coupler unit 208 which is provided at an end portion of the third single mode fiber 232 and is light-received as coherent light by the photo detector 210. The coherent light which is light-received by the photo detector 210 in this manner is photoelectrically converted and amplified by an amplifier 211.

Thereafter, the coherent and amplified light is inputted to a demodulator 212 which carries out a demodulation process for extracting only a signal component of the interfered light in the demodulator 212, and the output thereof is inputted to an A/D converter 213. In the A/D converter 213, there is produced digital data "coherent light data" of one line by sampling the coherent light signal, for example, for 200 points. In this case, the sampling frequency becomes a value dividing one scanning time period of the optical path length by 200.

The coherent light data per line unit which is produced by the A/D converter 213 is inputted to a signal processing unit 214. In the signal processing unit 214, by converting the coherent light data in the depth direction of the biological tissue to a video signal, there is generated a cross-sectional image at each position inside the blood vessel and it is outputted to the LCD monitor 113 at a predetermined frame rate. Also, the signal processing unit 214 is connected further with an optical path length adjuster control apparatus 226. The signal processing unit 214 carries out the control of the position of the one-axis stage 220 through the optical path length adjuster control apparatus 226. Also, the signal processing unit 214 is connected with a motor control circuit 225 and controls a rotary drive of the radial scanning motor 205. Further, the signal processing unit 214 is connected with a galvanometer controller 224 for controlling the scan of the optical path length of the reference mirror (galvanometer mirror) and the galvanometer controller 224 outputs a drive signal to the signal processing unit 214. In the motor control circuit 225, synchronization with the galvanometer controller 224 is achieved by using this drive signal. There is also included an injector 290 for injecting a flash liquid when imaging the cross-section and a communication unit 280 that carries out communication between the signal processing unit 214 and the injector 290.

3. Overall Construction of Optical Probe Unit 101

Figure 3:
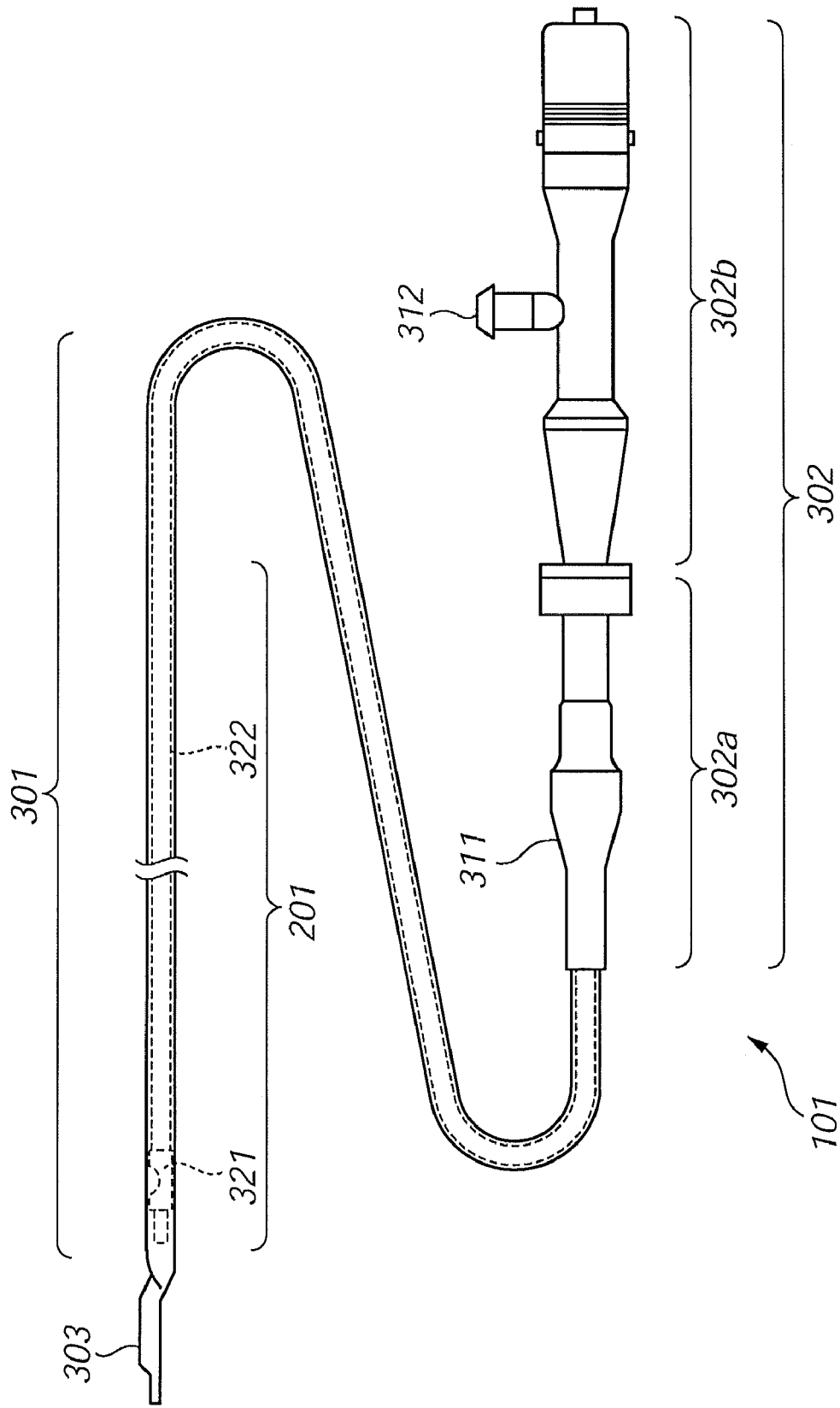
FIG. 3 is a perspective view of an optical probe used with the imaging diagnostic apparatus.

Referring to FIG. 3, the overall construction of the optical probe unit 101 is as follows. As shown in FIG. 3, the optical probe unit 101 is constituted by a long-sized catheter sheath 301 which is directly inserted inside a body lumen of a blood vessel or the like and a connector unit 302 which is not inserted inside the body lumen (i.e., the connector unit 302 is kept outside the body lumen) and which is arranged on the hand side of a user for the purpose of being steered by the user. At the distal end of the catheter sheath 301, there is formed a tube for guide wire lumen 303 and the catheter sheath 301 is formed with a lumen which is continuous from a connection portion with the connector unit 302 beyond a connection portion with the guide wire lumen tube 303.

In the lumen of the catheter sheath 301, there is passed-through, over almost the full length of the catheter sheath 301, the imaging core 201 including a housing 321 provided with a transmitting and receiving unit (401 in FIG. 4) for transmitting and receiving the measurement light and a drive shaft 322 for transmitting a drive force which makes it rotate. The linear drive apparatus 207 and the rotary drive apparatus 204 represent an example of a scanning drive unit that rotates and axially moves the transmitting and receiving unit 401. In this regard, the scanning drive unit is operatively connected to the transmitting and receiving unit 401 to effect such rotation and axial movement of the transmitting and receiving unit 401.

The connector unit 302 is composed of a hand-side unit 302a constituted integrally at a proximal end of the catheter sheath 301 and a connection connector 302b constituted integrally at a proximal end of the drive shaft 322. An anti-kink protector 311 is provided at a boundary portion of the hand-side unit 302a and the catheter sheath 301. Thus, a predetermined rigidity is maintained and it is possible to inhibit or prevent a bend (kink) caused by a rapid change. The proximal end of the connection connector 302b is connectable with the scanner & pull-back unit 102 which will be mentioned later. A reference numeral 312 indicates a port which is connected with the injector 290 and which is for injecting flash liquid into the lumen of an imaging target when imaging the cross-sectional image.

4. Construction of Distal End Portion of Optical Probe Unit

Figure 4:
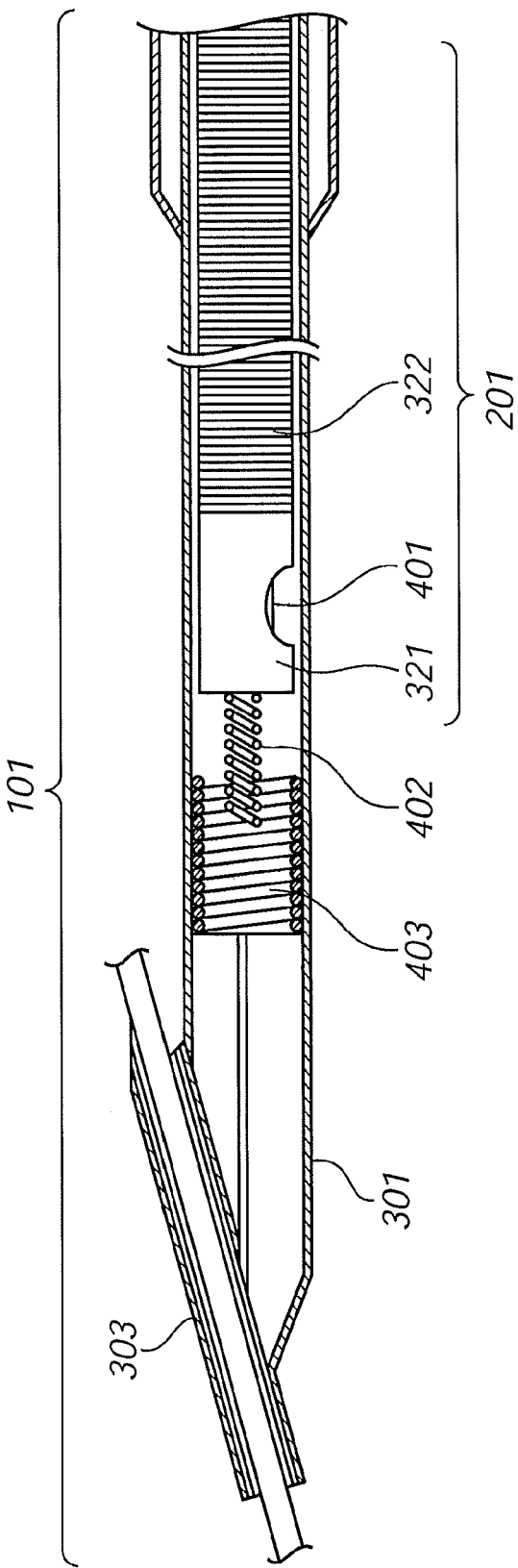
FIG. 4 is a longitudinal cross-section of the distal end portion of the optical probe.

Referring to FIG. 4, set forth below is an explanation of the construction of the distal end portion of the optical probe unit 101. As shown in FIG. 4, over almost the full length of the lumen of the catheter sheath 301, there is passed-through the imaging core 201 provided with the housing 321 arranged with the transmitting and receiving unit 401 for transmitting the measurement light and for receiving the reflected light and the drive shaft 322 for transmitting the drive force which makes it rotate, and the optical probe unit 101 is formed thereby. The transmitting and receiving unit 401 includes an optical mirror 601 and an optical lens 602 as mentioned later according to FIG. 6.

The transmitting and receiving unit 401 transmits the measurement light toward the biological tissue and concurrently, receives the reflected light from the biological tissue. The drive shaft 322 is formed in a coil shape and the optical fiber 231 of a single mode is arranged in the inside thereof.

The housing 321 is formed in a shape having a cutout portion at a portion of a short cylindrical metal pipe and it is formed by a cutting-out from a metal block, by an MIM (Metal powder Injection Molding) or the like. The housing 321 includes the transmitting and receiving unit 401 in the inside and the proximal end side thereof is connected with the drive shaft 322. Also, a short coil shaped flexible member 402 is provided on the distal end side thereof.

The flexible member 402 is a member in which a stainless steel wire member is formed in a coil shape and owing to a fact that the flexible member 402 is arranged on the distal end side, catching in the catheter sheath is inhibited prevented when the imaging core 201 is moved forward and backward. Reference numeral 403 indicates a reinforcement coil and is provided for the purpose of preventing the rapid bend of the distal end portion of the catheter sheath 301.

The tube for guide wire lumen 303 includes a lumen for the guide wire into which the guide wire is insertable. The tube for guide wire lumen 303 accepts the guide wire which is inserted inside the body lumen of the blood vessel or the like preliminarily by using the guiding catheter and it is used as a tube by which the catheter sheath 301 can be guided until a target lesion (cross-sectional image acquisition position) owing to the guide wire.

It is possible for the drive shaft 322 to make the transmitting and receiving unit 401 move rotatingly and move axially with respect to the catheter sheath 301, and it is constituted by a multiplex multi-layer contact coil or the like which is flexible and also has a characteristic of being able to relatively reliably transmit the rotation, and which is composed, for example, of a metal wire such as a stainless steel and the like.

It is possible for the drive shaft 322 to operate rotatingly and slidingly with respect to the catheter sheath 301, and it is constituted by a multiplex multi-layer contact coil or the like which is flexible and also has a characteristic of being able to relatively reliably transmit the rotation, and which is composed, for example, of a metal wire such as a stainless steel and the like. It become possible to observe the inside of the lumen for 360 degrees depending on the rotation of the drive shaft 322 and in order to observe a wider region, the drive shaft 322 is slidable axially.

Figure 5:
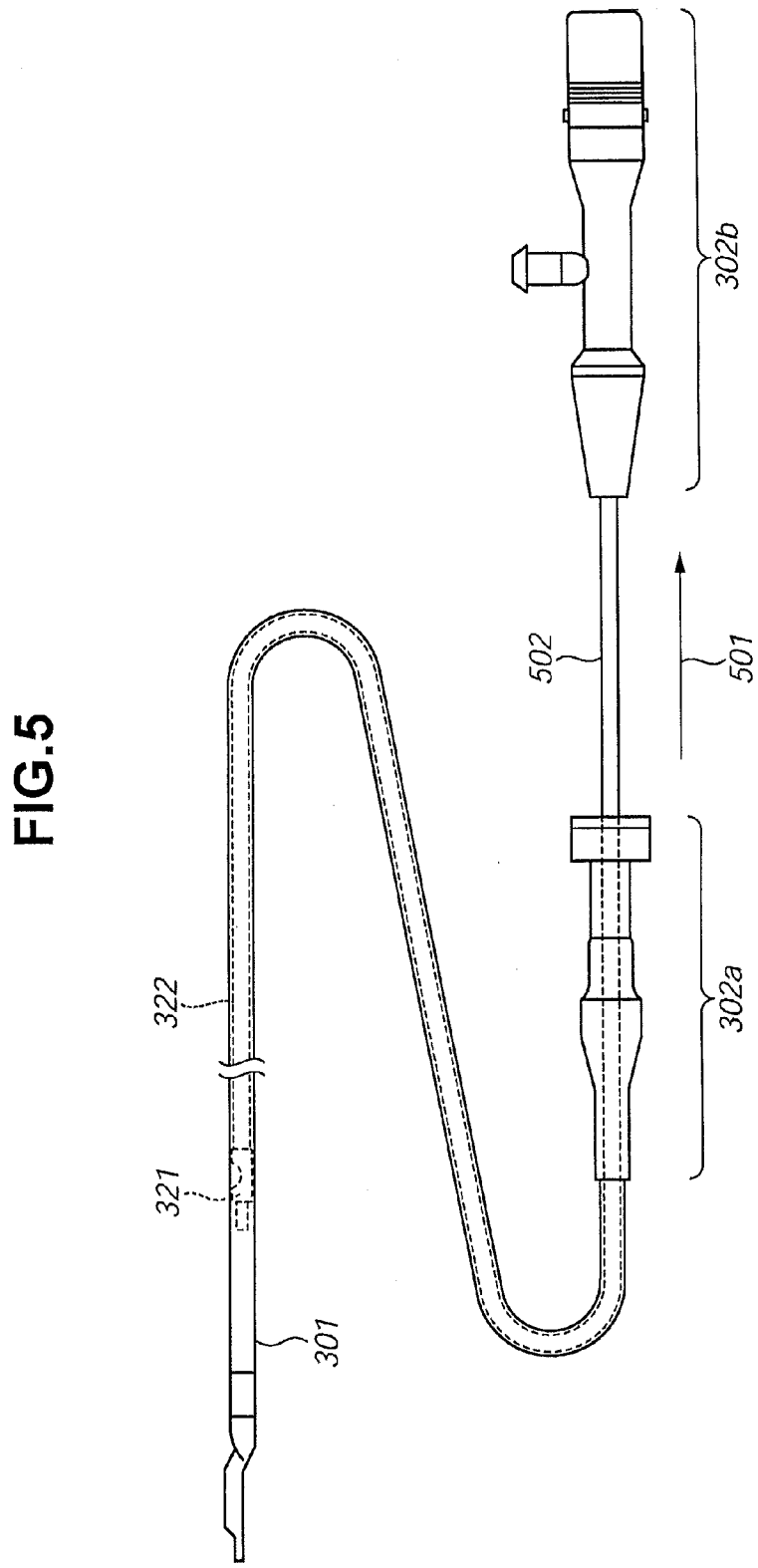
FIG. 5 is a perspective view of the optical probe in a state in which the drive shaft is slid in the optical probe relative to the catheter sheath.

FIG. 5 is a diagram showing an aspect (pull-back aspect) in which the drive shaft 322 is slid relatively with respect to the catheter sheath 301. As shown in the same drawing, if the connection connector 302b is slid toward the proximal end side (in the direction of the arrow 501) in a state in which the hand-side unit 302a is fixed, it happens that the inside drive shaft 322 and the housing 321 fixed at the distal end thereof are slid axially. It is possible for this sliding in the axial direction to be carried out manually by a user or to be carried out electrically, but it is assumed, in this example of one disclosed embodiment, that it is carried out depending on a linear drive motor included in the linear drive apparatus 207 under the control of the signal processing unit 214. It should be noted that a protection inner tube 502 is provided on the distal end side of the connection connector 302b such that the drive shaft 322 which rotates at a relatively high-speed is not exposed.

5. Operation of Optical Probe Unit 101

Figure 6:
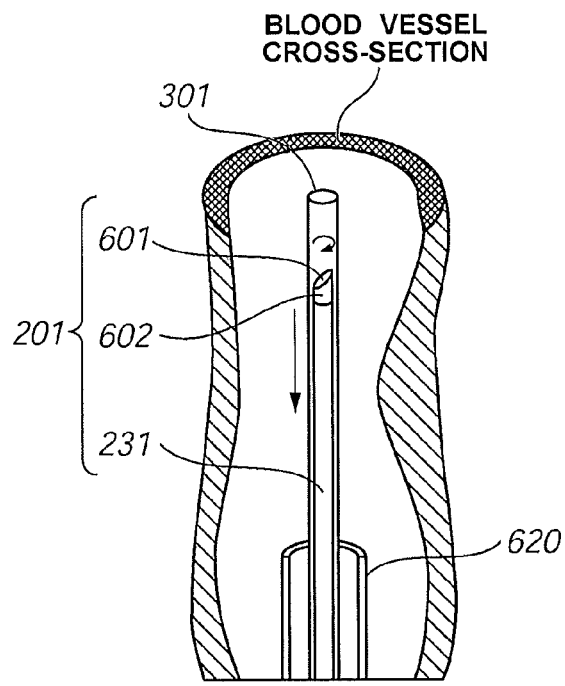
FIG. 6 is a schematic diagram explaining a rotation scan and an axial-direction movement by an optical probe in a blood vessel.
Figure 7:
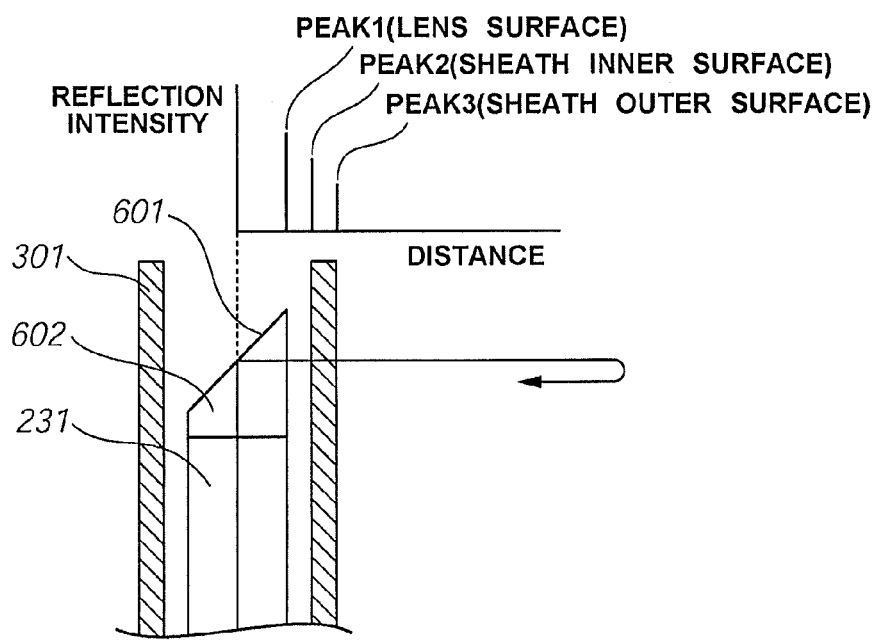
FIG. 7 is a diagram explaining illumination of measurement light and reflected-light intensity thereof.

In the inside of the imaging core 201 having the housing 321 and the drive shaft 322, there is arranged, as shown in FIG. 6, the optical fiber 231 whose distal end is attached with the optical mirror 601 and the optical lens 602. Then, the radial scan is carried out by rotating the optical mirror 601 and the optical fiber 231. As shown in FIG. 7, in a state in which the optical probe unit 101 is inserted into a blood vessel, the light outputted from the low coherent light source 209 passes through the optical fiber 231, changes its direction caused by the optical mirror 601 at the distal end and is emitted from the distal end portion of the fiber toward the cross-section direction of the blood vessel. Then, the reflected light is inputted to the apparatus inside by way of the same distal end portion of the optical fiber 231. Then, the cross-sectional image of the blood vessel is obtained depending on the reflection intensity of this reflected light. Also, owing to a fact that the optical mirror 601 at the distal end is rotated toward the circumferential direction caused by the rotation of the radial scanning motor 205, it is possible to obtain reflected light of each direction at a predetermined position inside the blood vessel.

Figure 8A:
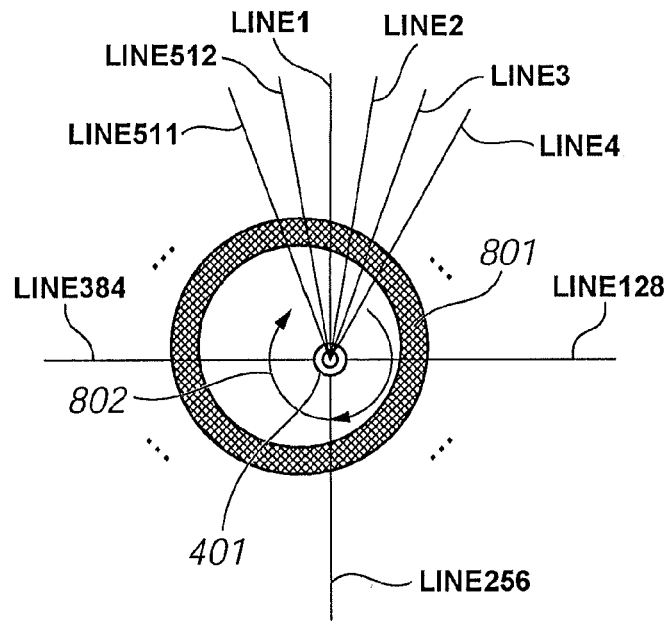
FIGS. 8A and 8B are schematic diagrams explaining an operation of an optical probe in a blood vessel.
Figure 8B:
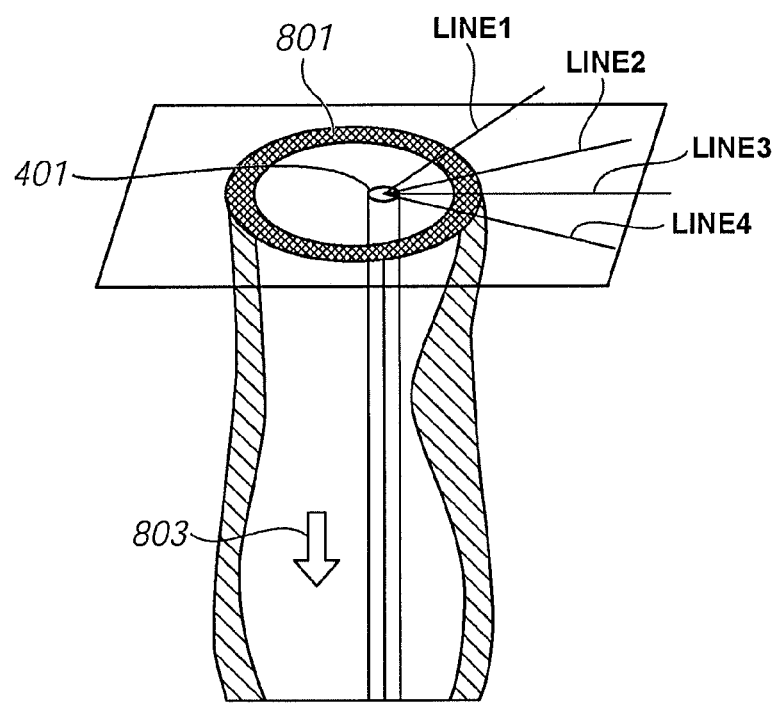

FIG. 8 is a schematic diagram explaining an operation of the optical probe unit 101 when imaging the blood vessel cross-sectional image. FIGS. 8A and 8B are a cross-sectional view and a perspective view of the blood vessel respectively in a state in which the optical probe unit 101 is inserted.

FIG. 8A illustrates the blood vessel 801 cross-section in which the optical probe unit 101 is inserted. As mentioned above, the optical probe unit 101 is attached with the optical lens 602 and the optical mirror 601 at the distal end thereof, and it is rotated by the radial scanning motor 205 in the direction of the arrow 802.

The transmitting and receiving of the measurement light is carried out by each rotary angle depending on the optical lens 602. Lines 1, 2, . . . , 512 show the transmitting direction of the measurement light at each rotary angle. In this embodiment, 512 times of transmitting and receiving of the measurement light are carried out intermittently during the time when the transmitting and receiving unit 401 including the optical mirror 601 and the optical lens 602 rotates 360 degrees at the position (axial position) of a predetermined blood vessel cross-section 801. The number times of transmitting and receiving of the measurement light during the period for rotating 360 degrees (one complete rotation) are not limited in particular by this aspect and it is assumed to be optionally settable. In this manner, the scan (SCAN) which repeats the transmitting and receiving of the signal while rotating the transmitting and receiving unit 401 is generally referred to as "radial scan (radial SCAN, rotation scan)".

Also, the transmitting of the measurement light and the receiving of the reflection light depending on such a transmitting and receiving unit 401 are carried out while the transmitting and receiving unit 401 is advanced inside the blood vessel in the direction of the 803 in FIG. 8B.

6. Construction and Operation of Signal Processing Unit 214

Figure 9:
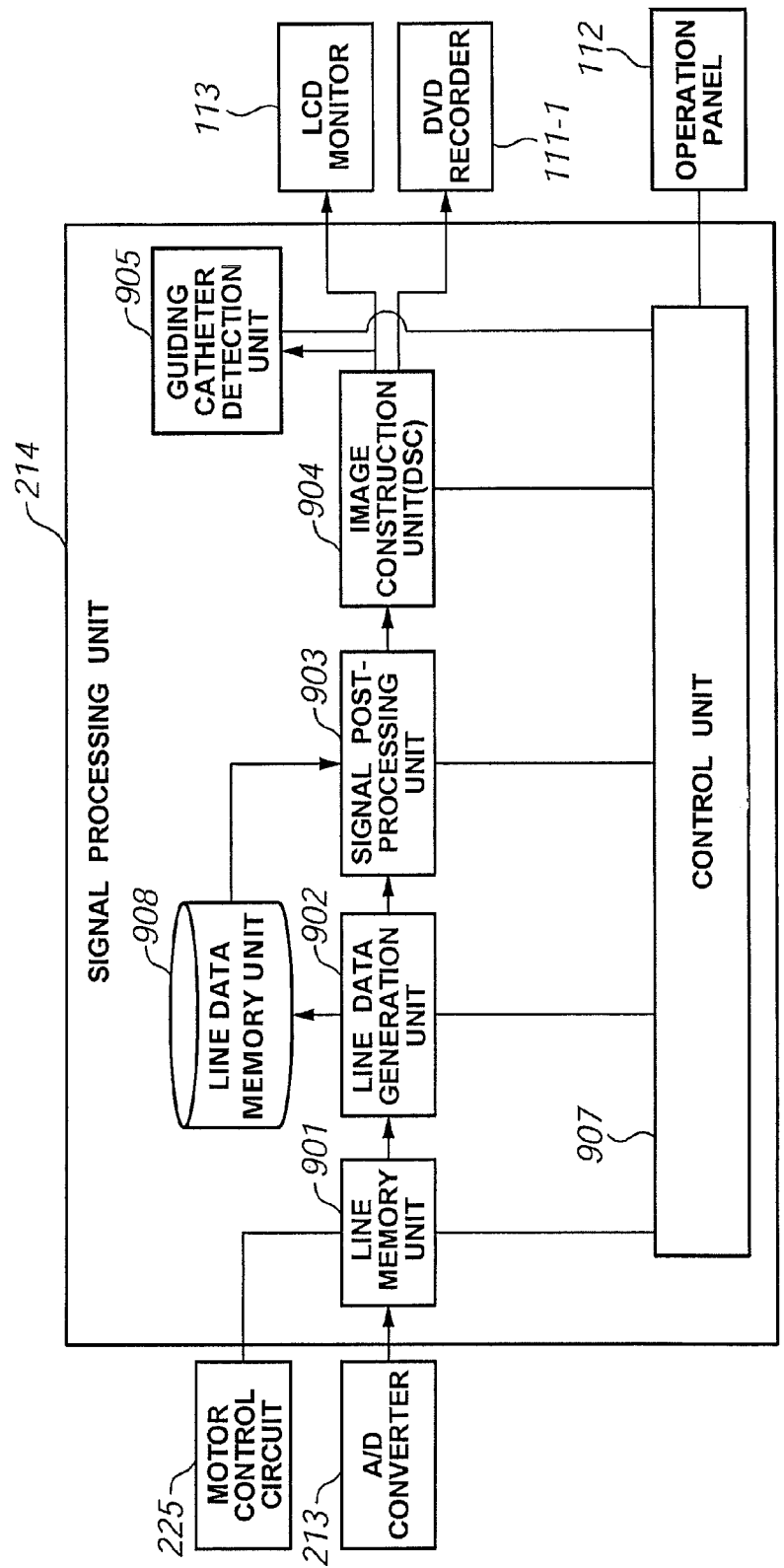
FIG. 9 is a block diagram of a signal processing unit.

Referring to FIG. 9, set forth below is a description outlining a process in the signal processing unit 214 of the imaging diagnostic apparatus 100. FIG. 9 is a diagram schematically showing a detailed construction of the signal processing unit 214 and functional blocks related thereto.

As mentioned above, the photo coupler unit 208 produces coherent light from the reflected light inputted through the optical fiber 231 and the reference light transmitted in the third single mode fiber 232. The interference intensity of the produced coherent light is converted to an electric signal by the photo detector 210, the amplifier 211 and the demodulator 212 and it is supplied to the A/D converter 213. Here, with respect to the reference light, the optical path length of about 3 mm is scanned depending on the galvanometer 217 which is a mirror for changing the optical path length. More specifically, it happens that the reflection intensity from each depth inside the biological tissue is to be scanned depending on the scan of the optical path length of the reference light. Here, the reason why the scan range is set to be 3 mm is because the drawing-out is carried out until the depth of 3 mm, though it is not particularly limited by that value.

In the A/D converter 213, there is produced digital data of one line by sampling the signal outputted from the demodulator 212 for 200 points. At that time, the sampling frequency is assumed to be a value dividing one scanning time period of the optical path length by 200. In this manner, it is possible to obtain digital data of 200 points with respect to the depth of 3 mm. However, it can be determined also with respect to a different number of points of these data depending on the process method carried out in the succeeding stage, so that it is not limited by that value. The digital data (optical coherence data) produced by the A/D converter 213 is outputted to the signal processing unit 214.

The coherent light data produced by the A/D converter 213 is, first, supplied to a line memory unit 901. In the line memory unit 901, the number of lines per one rotation of the transmitting and receiving unit 401 is processed so as to become 512 lines based on an encoder signal of the motor which is outputted from the motor control circuit 225 and it is outputted to the line data generation unit in the succeeding stage.

A line data generation unit 902 generates the line data owing to a fact that a line addition-averaging process, a filtering process, a logarithmic conversion process and the like are applied with respect to the coherent light data and the coherent light intensity data in the depth direction of the biological tissue is generated. The generated line data are stored in a line data memory unit 908. The line data generation unit 902 together with the line data memory unit 908 represent an example of a generating and holding means for generating data, corresponding to the cross-sectional image, and for holding such data. As discussed previously, the cross-sectional image-creating data is generated using the coherent light between the reflected light obtained through the transmitting and receiving unit and the reference light. It should be noted in this example of the disclosed embodiment that, for example, the line data for one screen (for one rotation of the transmitting and receiving unit 401), that is, the line data of 512 lines are obtained by 160 fps (frames per second) and they are stored in the line data memory unit 908. Also, the line data generation unit 902 outputs the line data to a signal post-processing unit 903 in the succeeding stage in order to generate a two-dimensional image for being displayed on the LCD monitor 113 by a pace of 30 fps. Therefore, in this embodiment, the two-dimensional image for the monitor is generated by a rate of 30 fps within the data obtained by 160 fps owing to the radial scan and the pull-back scan, and the display is carried out on the LCD monitor 113 in real time. It should be noted that the values of 160 fps or 30 fps only represent an example and are not to be viewed as being limited in this regard.

In the signal post-processing unit 903, a contrast adjustment, an intensity adjustment, a gamma correction, a frame correlation, a sharpness process and the like are carried out with respect to the line data and the processed line data are outputted to an image construction unit 904 (DSC). In the image construction unit 904, a two dimensional cross-sectional image is generated owing to a fact that the line data series of the polar coordinate are Re-converted and thereafter, it is converted to the video signal and displayed on the LCD monitor 113 as the blood vessel cross-sectional image. A guiding catheter detection unit 905 detects the guiding catheter from the image generated by the image construction unit 904 and judges whether or not the transmitting and receiving unit 401 has entered the lumen of the guiding catheter. Then, the guiding catheter detection unit 905 notifies that effect to the control unit 907 in a case in which it is judged that the transmitting and receiving unit 401 has entered the lumen of the guiding catheter. It should be noted in this embodiment that the cross-sectional image generated by 512 lines of data is just one example, and is not limited by that number of lines. Also, a control unit 907 comprehensively controls each portion mentioned above and the guiding catheter detection unit 905 explained hereinafter.

Also, after finishing the pull-back scan, the control unit 907 controls the signal post-processing unit 903 and the image construction unit 904 in response to a user's instruction from the operation panel 112, and the two-dimensional image is generated from the line data stored in the line data memory unit 908 and it is recorded in the DVD recorder 111-1 or the like.

Figure 10A:
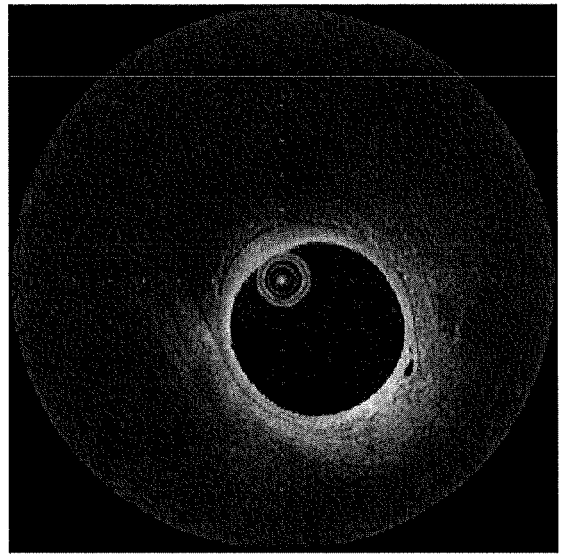
FIGS. 10A and 10B are diagrams showing examples of a cross-sectional image of a blood vessel lumen and a cross-sectional image of a guiding catheter lumen respectively.
Figure 10B:
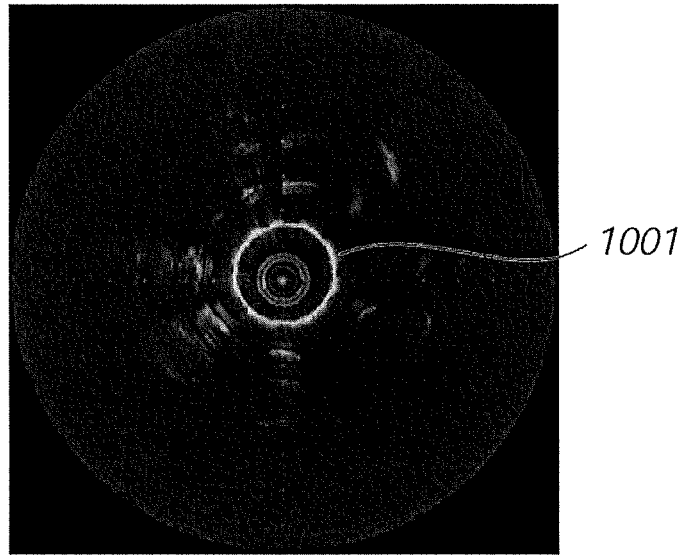

Set forth below is a description of the process of the guiding catheter detection unit 905 which is produced by the image construction unit 904. An example of the cross-sectional image obtained by the optical coherent tomography apparatus is shown in FIG. 10. FIG. 10A shows a state in which the transmitting and receiving unit 401 is exposed from the guiding catheter and it can be understood that the image of the lumen of the blood vessel is obtained. On the other hand, FIG. 10B shows a cross-sectional image obtained in a state in which the transmitting and receiving unit 401 entered into the lumen of the guiding catheter. With respect to the guiding catheter, a shape in which a metallic blade is braided into a plastic tube is general. As is clear from the image of FIG. 10B, the shape of the guiding catheter is regular and a diameter thereof is small compared with that of the blood vessel, so that it is possible to distinguish an image 1001 of the guiding catheter easily from the blood vessel by tracing the high intensity portion. For example, the intensity is plotted from the screen center toward the radiation direction and the place where the differential component thereof is large is assumed to be the lumen. The lumen is plotted toward the circumferential direction and a case in which a circle can be drawn seamlessly is assumed to be the guiding catheter.

It should be noted that the detection algorithm of the guiding catheter mentioned above is merely one example and it is not limited in this regard. For example, the following can be true.

In a case in which a ring of a predetermined diameter (diameter of guiding catheter) is detected by plotting the regions of a predetermined intensity value or more, it is judged that the ring is the guiding catheter.

In a case in which a ring of a predetermined intensity value or more is detected and the intensity of the outside of the ring becomes a predetermined value or less (in a case in which the outside of a ring cannot be observed), it is also possible to use such a judgment method by which it is judged that the ring is the guiding catheter.

Alternatively, it is also possible to use plural kinds of judgment methods in combination. Further, it is also possible to judge that the transmitting and receiving unit 401 entered in the lumen of the guiding catheter in a case in which it is judged that the guiding catheter is detected from the image is continued over a plurality of frames. Also, in a case in which it is judged that the transmitting and receiving unit 401 entered in the lumen of the guiding catheter, the generation and the storage of the line data are stopped and concurrently, it is also possible to stop the radial scan and the pull-back scan.

Figure 11:
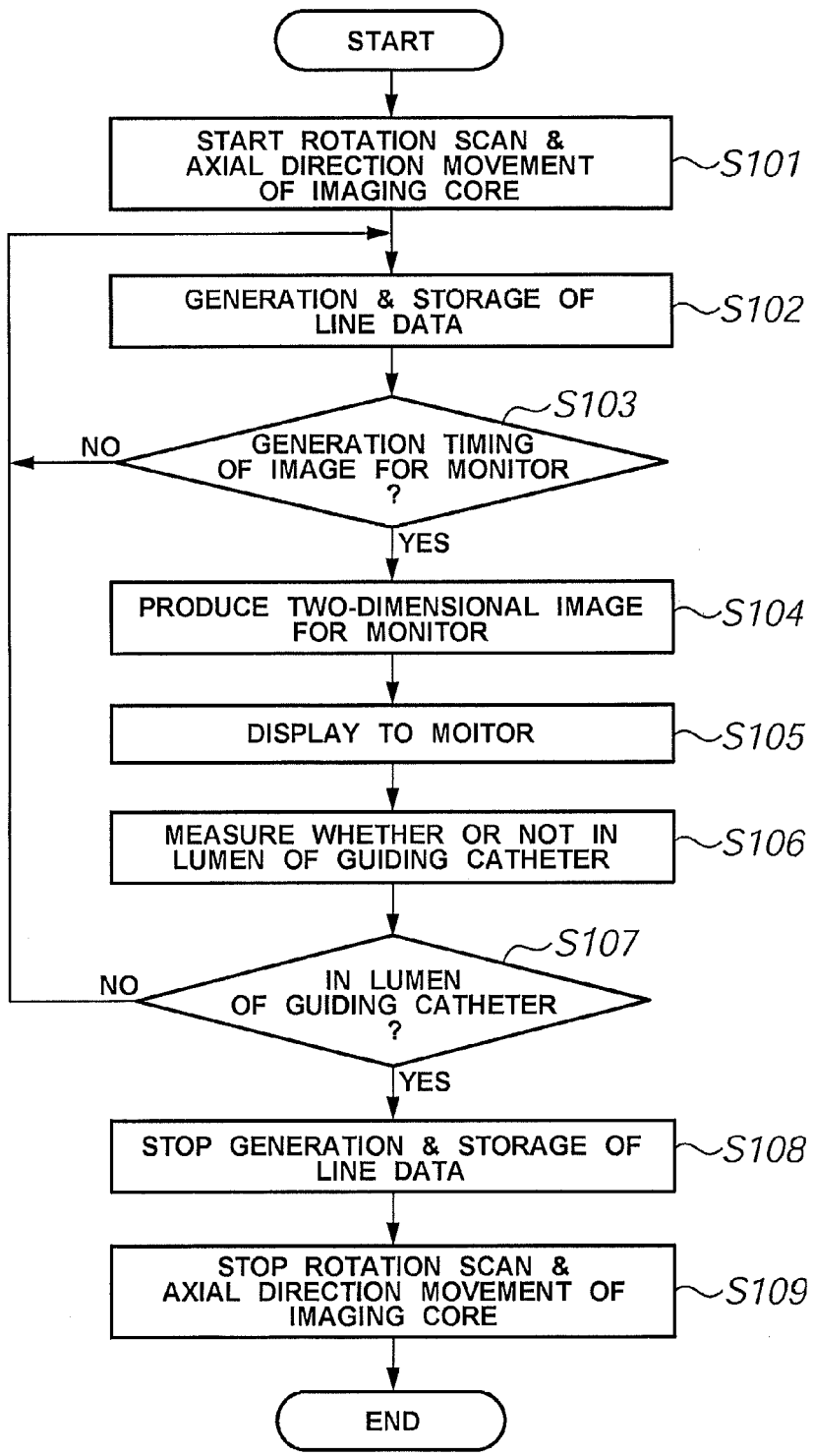
FIG. 11 is a flowchart explaining a cross-sectional image acquisition process according to an embodiment disclosed by way of example

FIG. 11 is a flowchart explaining an optical coherence cross-sectional image acquisition process performed by the signal processing unit 214 according to this embodiment described by way of one example. In response to an imaging start instruction to the operation panel 112 from a user, the control unit 907 carries out a drive instruction with respect to the motor control circuit 225 and the linear drive apparatus 207 and starts the rotation scan and the axial-direction movement of the imaging core 201 (S101). It should be noted in this embodiment that it is assumed that the supply of the flash liquid is allowed to be carried out either by a manual operation or by an automatic operation.

When the rotation scan is started, as mentioned above, the line memory unit 901 and the line data generation unit 902 generate the line data and store the data in the line data memory unit 908 (S102). In this embodiment, as mentioned above, it is assumed that the line data are generated at, for example, 160 frames per second (160 fps).

Also, in this embodiment, the image during the imaging period is displayed on the LCD monitor 113 in real time, but it is assumed that the image displayed on the LCD monitor 113 is 30 frames per second (30 fps). In this embodiment, the detection of the guiding catheter is carried out by utilizing the image used for this display. However, the image displayed in real time during the imaging period is not used for diagnosis, so it is possible apply lower resolution to the image, compared to the resolution which the line data has. Also in such a case, it is possible for the detection of the guiding catheter of this embodiment to be carried out. The control unit 907 judges whether or not it is the timing for generating the two-dimensional image for the monitor display and the process will return to S102 if it is not the timing for generating the two-dimensional image (S103). On the other hand, if it is time for generating the two-dimensional image, the process proceeds to S104. It should be noted that also during the processes of S104 to S107 explained hereinafter, the generation and the storage of the line data by the line memory unit 901 and the line data generation unit 902 are carried out continuously.

When it becomes time to carry out image generation for the monitor, in response to the instruction of the control unit 907, the line data generation unit 902 stores the line data in the line data memory unit 908 and concurrently, transmits the data to the signal post-processing unit 903. Then, the signal post-processing unit 903 and the image construction unit 904 generate a two-dimensional image for being displayed on the LCD monitor 113 (S104) and the generated image is displayed on the LCD monitor 113 (S105). Also, the guiding catheter detection unit 905 judges whether or not the transmitting and receiving unit 401 enters in the lumen of the guiding catheter 620 by detecting the image of the guiding catheter from the two-dimensional image for the monitor which is generated in step S104 (S106). Then, in a case in which it is judged that the unit has not entered the lumen of the guiding catheter, the process returns to S102 and the process mentioned above is repeated (S107). On the other hand, in a case in which it is judged in step S106 that the transmitting and receiving unit 401 enters the lumen of the guiding catheter, the control unit 907 stops at least a portion of the processes relating to the processes from the generation to the holding of the optical coherence cross-sectional image (data). In this embodiment, for example, the generation and the storage of the line data by the line memory unit 901 and the line data generation unit 902 are stopped (S107, S108). Then, the control unit 907 stops the rotation scan and the axial-direction movement of the imaging core 201 (S109). At the time when the transmitting and receiving unit 401 are determined to have entered the guiding catheter, the transmitting and receiving unit 401 is still capable of pull-back movement (i.e., the transmitting and receiving unit 401 has not yet reached its most pulled-back position).

Figure 12:
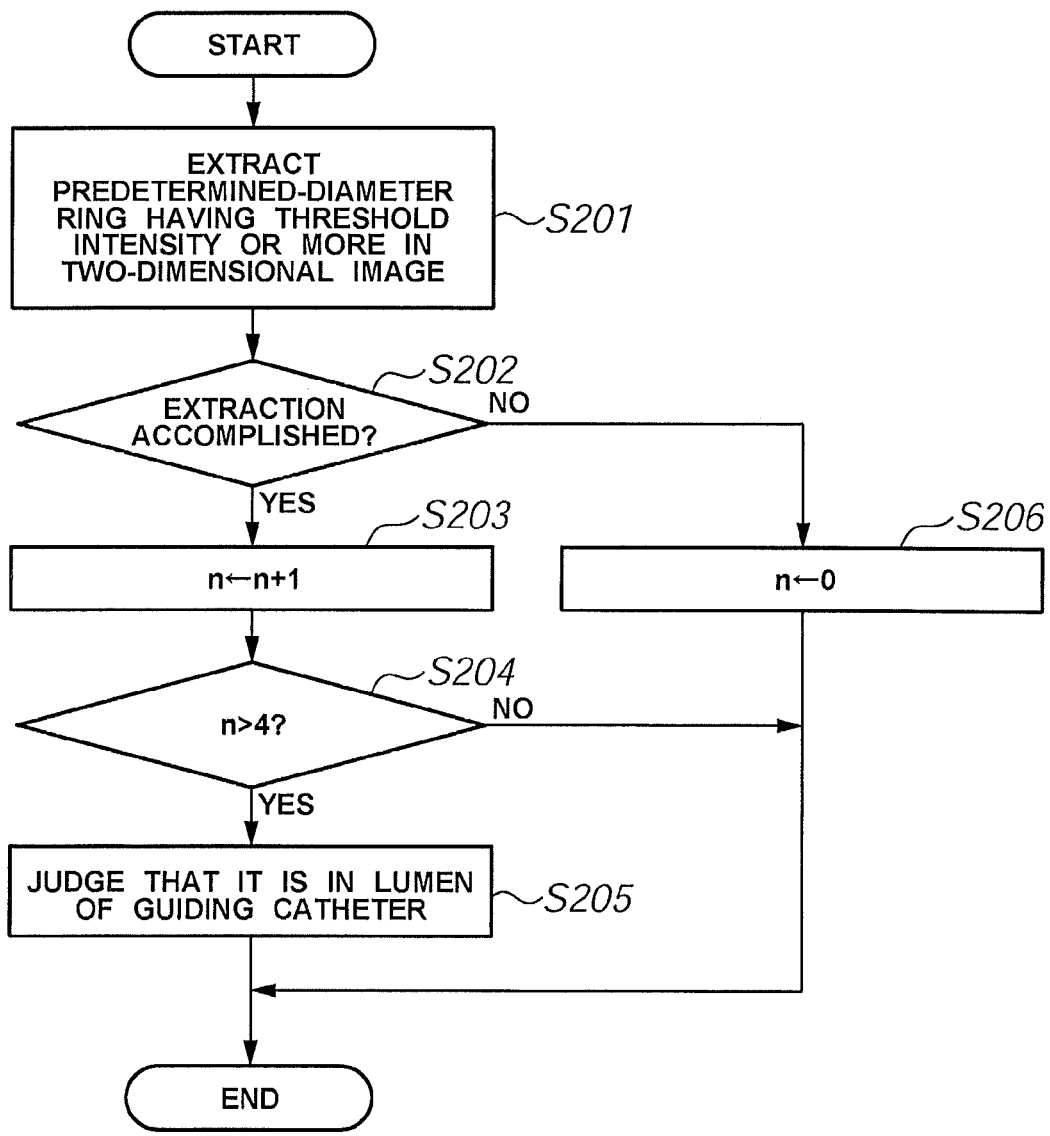
FIG. 12 is a flowchart showing a process for detecting that a transmitting and receiving unit of an optical probe exists in a guiding catheter lumen.

FIG. 12 is a flow chart showing one example of the process (judgment of whether or not the transmitting and receiving unit 401 exists in the lumen of the guiding catheter) performed by the signal processing unit 214 in step S106 of FIG. 11. The guiding catheter detection unit 905 detects, depending on the method mentioned above, the image of the guiding catheter from the two-dimensional image which the image construction unit 904 generates as the image for the monitor. For example, portions of the image having the intensity of a threshold value or more are traced in the two-dimensional image and a ring having a predetermined diameter is extracted. Here, the predetermined diameter means a diameter corresponding to the inner diameter of the guiding catheter 620. It is possible for this predetermined diameter to be set so as to have a tolerance range. In a case in which the ring of a predetermined diameter can be extracted in step S201, parameter n is incremented by 1 (S202, S203). Then, in a case in which the n becomes greater than 4, it is judged that the two dimensional image is in the lumen of the guiding catheter (that is, the transmitting and receiving unit 401 exists in the lumen of the guiding catheter 620) (S204, S205). On the other hand, in a case in which the ring of a predetermined diameter cannot be extracted in step S201, the parameter n is set to be zero (S202, S206). According to the process mentioned above, in a case in which the ring of a predetermined diameter is extracted continuously by five times, it is judged that the transmitting and receiving unit 401 exists in the lumen of the guiding catheter. Here, it is judged in FIG. 12 that the unit is in the lumen of the guiding catheter in a case in which the ring of a predetermined diameter (image of the guiding catheter) is detected continuously five times (or more), but this number of times may be different. For example, it is possible to stop the generation and the storage of the line data when the guiding catheter is detected even only once. It is also possible in step S109 to employ a construction for stopping the injection of the flash liquid by the injector 290.

As mentioned above, according to the first embodiment disclosed by way of example here, the acquisition of the data is stopped in response to detecting that the transmitting and receiving unit for the measurement light and the reflected light enters in the lumen of the guiding catheter, so that it is possible to prevent the acquisition of useless data. Also, the image generated for the monitor is commonly used for the detection of the guiding catheter, so that it is not necessary to generate the two-dimensional image separately for the detection. Also, as mentioned above, in case of employing a construction in which the two-dimensional image is generated for a real time display by reducing the resolution thereof, the extraction of the guiding catheter is carried out based on the two-dimensional image of low resolution, so that the amount of calculations is reduced. It should be noted with respect to the guiding catheter that the shape thereof is regular and also high intensity is obtained, so that the detection is comparatively easily accomplished and it is possible to carry out the detection even from the two-dimensional image of low resolution for the real time display.

Second Embodiment

In a second example of an embodiment of the apparatus and method disclosed here, the signal processing unit 214 of the optical coherent tomography apparatus (OCT apparatus) communicates with the injector 290 for injecting the flash liquid through the communication unit 280 and controls the start and the stop of the flash liquid. More specifically, when it is judged by the guiding catheter detection unit 905 that the transmitting and receiving unit 401 has entered the lumen of the guiding catheter, the control unit 907 of the signal processing unit 214 carries out communication with the injector 290 through the communication unit 280 and stops the injection of the flash liquid. For example, the injection of the flash liquid is started with respect to the injector 290 in step S101 of FIG. 11 and the injection of the flash liquid is stopped in step S108. More specifically, in this second embodiment, a portion of the processes relating to the processes from the generation to the holding of the optical coherence cross-sectional image, which is stopped in response to the detection that the transmitting and receiving unit 401 has entered the lumen of the guiding catheter, is made to be the injection of the flash liquid. It should be noted that with respect to the communication standard of the interface which the communication unit 280 includes, it is possible to employ a serial communication using RS-232C, USB or the like and it is also possible to employ a signal of exclusive use, in which there is no limitation by the communication standard. In addition, in case of seeking to inhibit or prevent unnecessary or needless injection of the flash liquid, it is optional for the process whether or not the generation and the storage of the line data are stopped in step S108.

Third Embodiment

As mentioned above, in the first and the second examples of disclosed embodiments, there is used the optical coherent tomography apparatus (OCT apparatus) in which the optical path length of the reference light is scanned and the reflection intensity distribution in the depth direction is obtained. It is also possible, however, to apply the disclosure here to the optical frequency domain imaging apparatus utilizing the wavelength sweep. The third embodiment will be described with respect to a case in which the optical frequency domain imaging apparatus using the wavelength sweep is used for the imaging diagnostic apparatus.

Figure 13:
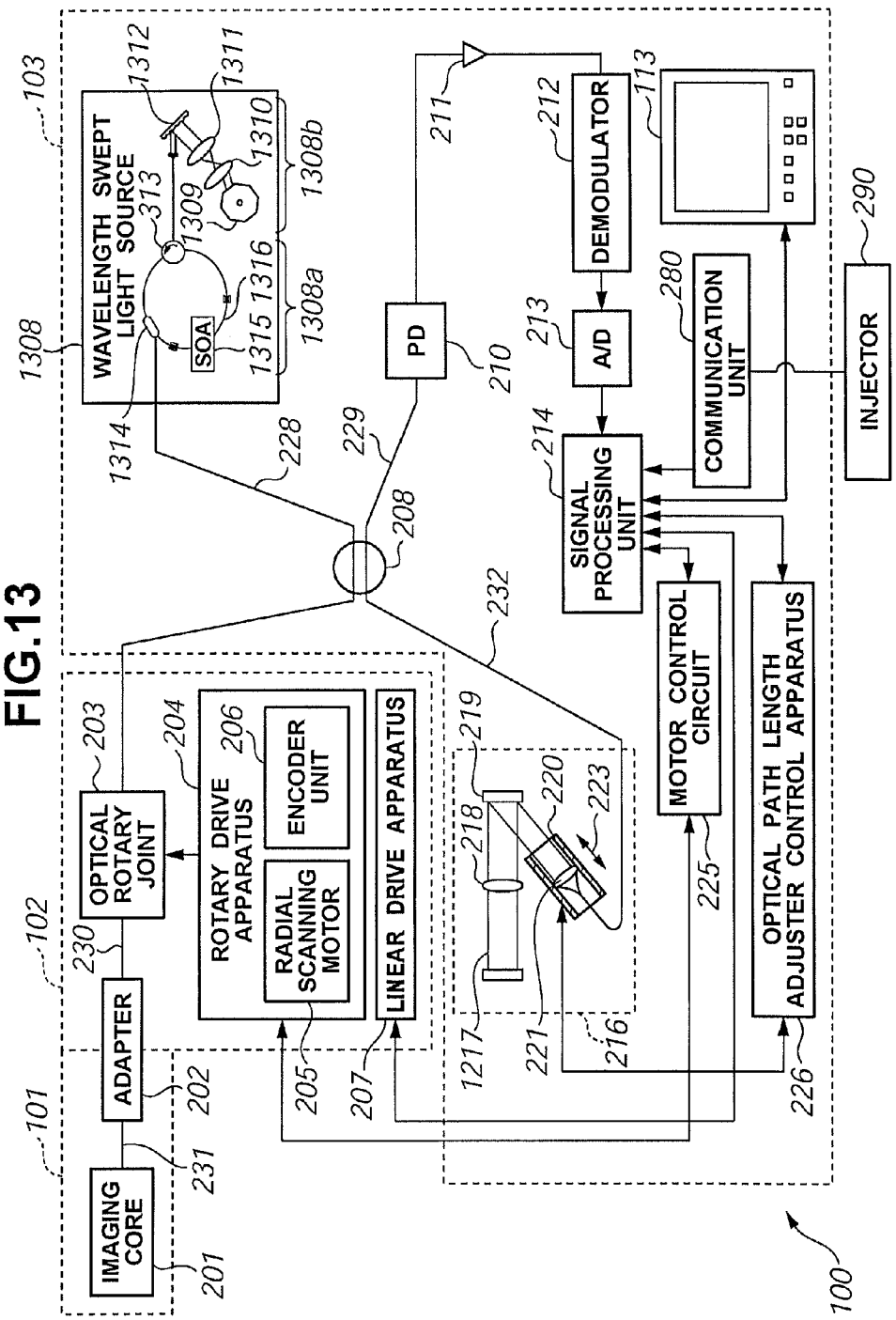
FIG. 13 is a block diagram of an optical frequency domain imaging apparatus utilizing wavelength sweep.

In FIG. 13, reference numeral 1308 indicates a wavelength swept light source and a Swept-Laser is used therein. The wavelength swept light source 1308 using the Swept-Laser is one kind of an Extended-Cavity Laser and it is composed of a light source unit 1308a having an optical fiber 1316 coupled in a ring shape with a SOA1315 (Semiconductor Optical Amplifier) and a polygon scanning filter 1308b. The light outputted from the SOA1315 proceeds to the optical fiber 1316 and enters in the polygon scanning filter 1308b, and the light whose wavelength is selected here is amplified by the SOA1315 and is finally outputted from a coupler 1314.

In the polygon scanning filter 1308b, the wavelength is selected by the combination of a diffraction lattice 1312 which light-splits the light and a polygon mirror 1309. Specifically, the light which is light-split by the diffraction lattice 1312 is focused on the surface of the polygon mirror 1309 by two pieces of lenses (1310, 1311). Thus, only the light having the wavelength, which is perpendicular to the polygon mirror 1309 returns to the same optical path and it happens that it is outputted from the polygon scanning filter 1308b, so that it is possible to carry out the time sweep of the wavelength by rotating the polygon mirror 1309. With respect to the polygon mirror 1309, for example, an icosadodecahedron mirror is used and the rotation speed thereof is around 50000 rpm. Owing to the wavelength sweep system in which the polygon mirror 1309 and the diffraction lattice 1312 are combined, it is possible to employ the wavelength sweep of high speed and high power. The light of the wavelength swept light source 1308, which is outputted from the coupler 1314 is entered into one end of the first single mode fiber 228.

Also, the scan of the optical path length is not necessary in the imaging diagnostic apparatus 100 utilizing the wavelength sweep, so that in the variable mechanism 216, there is provided a fixed mirror 1217 instead of the galvanometer 217.

As explained with respect to the first embodiment, the coherent light between the reflected light and the reference light is produced in the photo coupler unit 208 and an electric signal in response to the coherent light is produced by the photo detector 210. In the A/D converter 213, there are produced digital data of one line (coherent light data) by sampling the coherent light signal, for example, for 2048 points by 180 MHz. It should be noted that the reason why the sampling frequency is set to be 180 MHz is because it is on the assumption that about 90% of the cycle (12.5 µsec) of the wavelength sweep is to be extracted as the digital data of 2048 points in case of setting the repeat frequency of the wavelength sweep to be 80 kHz, though the disclosure is not especially limited in this respect.

The coherent light data per line unit produced in the A/D converter 213 is inputted to the signal processing unit 214. In the line memory unit 901 of the signal processing unit 214, the number of lines per one rotation of the transmitting and receiving unit 401 depending on the radial scanning motor is processed so as to become 512 lines and thereafter, it is outputted to the line data generation unit 902 in the succeeding stage. The line data generation unit 902 carries out the FFT (high speed Fourier conversion) with respect to the coherent light data and generates data in the depth direction by frequency-decomposition. More specifically, it is possible to obtain data in the depth direction without carrying out the scan of the optical path length, so that it becomes possible to accomplish the data acquisition of high speed compared with that of the OCT apparatus of the first embodiment. Then, because the coherent light intensity data is generated in the depth direction of the biological tissue by applying a line addition-averaging process, a filtering process, a logarithmic conversion process and the like, the line data are generated and the generated line data are stored in the line data memory unit 908 and concurrently, the data are supplied to the signal post-processing unit 903 if it is necessary. The processes thereafter are similar as those of the first embodiment.

Therefore, it is possible to apply the process explained in the first embodiment and the second embodiment to the imaging diagnostic apparatus 100 utilizing the wavelength sweep and it is possible to obtain effects similar to those explained above.

In the first embodiment, the recording of useless or unnecessary image was avoided or prevented by stopping the generation and the storage of the line data, but the disclosure here is not limited in this respect. For example, in a situation in which it is detected that the transmitting and receiving unit 401 has entered the guiding catheter, it is possible to add predetermined mark information to the line data which the line data generation unit 902 generated, and when recording the image on the DVD recorder 111-1, the image recording is prohibited with respect to the line data added subsequent to the line data provided with the mark information.

As explained above, according to the respective embodiments described above, it is possible to reduce the recording of unnecessary information and/or to reduce the injection of unnecessary flash liquid.

The detailed description above describes features and aspects of embodiments of an optical coherent cross-sectional image forming apparatus and associated control method. The invention is not limited, however, to the precise embodiments and variations described. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

What is claimed is:

1. An optical coherent cross-sectional image forming apparatus in which light outputted from a light source is divided into a measurement light and a reference light inside the apparatus and in which a cross-sectional image is formed based on a coherent light obtained from reflected light, acquired when the measurement light emitted toward a biological tissue through a probe inserted into a body lumen is reflected, and the reference light, the apparatus comprising:

a transmitting and receiving unit at a distal end portion of the probe, the transmitting and receiving unit emitting the measurement light and also receiving the reflected light, the transmitting and receiving unit being axially movable relative to a catheter sheath during operation of the apparatus;

a scanning drive unit connected to the transmitting and receiving unit to rotate and axially move the transmitting and receiving unit;

generating and holding means for generating data, corresponding to the cross-sectional image, using the coherent light between the reflected light obtained through the transmitting and receiving unit and the reference light, and for holding the data;

means for detecting, through use of the data held by the generating and holding means, that the transmitting and receiving unit has entered inside the catheter sheath during the axial movement; and a controller for stopping at least a portion of an operational aspect of the apparatus, from when the data corresponding to the cross-sectional image is generated to when the data is held, whenever the means for detecting detects that the transmitting and receiving unit has entered the catheter sheath.

2. The optical coherent cross-sectional image forming apparatus according to claim 1, wherein when the means for detecting detects that the transmitting and receiving unit has entered inside the catheter sheath, the controller controls the generating and holding means so as to stop holding the data.

3. The optical coherent cross-sectional image forming apparatus according to claim 1, wherein when the means for detecting detects that the transmitting and receiving unit has entered inside the catheter sheath, the controller stops injection of flash liquid to a vicinity of the transmitting and receiving unit.

4. The optical coherent cross-sectional image forming apparatus according to claim 1, wherein when the means for detecting detects that the transmitting and receiving unit has entered inside the catheter sheath, the controller controls the scanning drive unit to stop rotating and axially moving the transmitting and receiving unit.

5. The optical coherent cross-sectional image forming apparatus according to claim 1, further comprising:
   a construction unit for constructing a two-dimensional image for real time display from the data held by the generating and holding means; and wherein
   the means for detecting detects that the transmitting and receiving unit has entered inside the catheter sheath by extracting an image of the guiding catheter from the two-dimensional image constructed by the construction unit.

6. An optical coherent cross-sectional image forming apparatus in which light outputted from a light source is divided into a measurement light and a reference light inside the apparatus and in which a cross-sectional image is formed based on a coherent light obtained from reflected light, acquired when the measurement light emitted toward a biological tissue through a probe inserted into a body lumen is reflected, and the reference light, the apparatus comprising:
   an optical fiber connected to the light source, the optical fiber possessing a distal end portion which transmits the measurement light and also receives the reflected light;
   the optical fiber being positioned inside a catheter sheath, the optical fiber being rotatable within the catheter sheath, the optical fiber also being axially movable within the guiding catheter to axially move the optical fiber;
   a scanning drive unit connected to the optical fiber to rotate and axially move the optical fiber relative to the catheter sheath to axially move the distal and portion of the optical fiber into the catheter sheath;
   generating and holding means for generating and then holding data which is based on the coherent light and which is used to produce the cross-sectional image;
   means for determining that the distal end portion of the optical fiber which transmits the measurement light and also receives the reflected light has moved from a position outside the catheter sheath to a position inside the catheter sheath so that the distal end portion of the optical fiber is inside the catheter sheath; and
   control means for stopping at least one of the generation of the data and the holding of the data whenever the means for determining determines that the distal end portion of the optical fiber which transmits the measurement light and also receives the reflected light has entered the catheter sheath.

7. The optical coherent cross-sectional image forming apparatus according to claim 6, wherein when the means for detecting detects that the transmitting and receiving unit has entered inside the catheter sheath, the controller controls the generating and holding means so as to stop holding the data.

8. The optical coherent cross-sectional image forming apparatus according to claim 6, wherein when the means for detecting detects that the transmitting and receiving unit has entered inside the catheter sheath, the controller stops injection of flash liquid to a vicinity of the transmitting and receiving unit.

9. The optical coherent cross-sectional image forming apparatus according to claim 6, wherein when the means for detecting detects that the transmitting and receiving unit has entered inside the catheter sheath, the controller controls the scanning drive unit to stop rotating and axially moving the transmitting and receiving unit.

10. The optical coherent cross-sectional image forming apparatus according to claim 7, further comprising:
    a construction unit for constructing a two-dimensional image for real time display from the data held by the generating and holding means; and wherein
    the means for determining determines that the optical fiber has entered inside the catheter sheath by extracting an image of the catheter sheath from the two-dimensional image constructed by the construction unit.

11. A method for controlling an optical coherent cross-sectional image forming apparatus in which light outputted from a light source is divided into a measurement light and a reference light inside the apparatus and in which a cross-sectional image is formed based on a coherent light obtained from reflected light, acquired when the measurement light emitted toward a biological tissue through a probe inserted into a body lumen is reflected, and the reference light, the method comprising:
    rotating and axially moving a transmitting and receiving unit at a distal end portion of the probe which emits the measurement light and receives the reflected light, the transmitting and receiving unit being axially moved relative to a guiding catheter;
    generating data corresponding to the cross-sectional image using the coherent light and holding the data in a memory unit;
    determining when the transmitting and receiving unit has entered inside the guiding catheter during the axial movement of the transmitting and receiving unit; and
    stopping at least a portion of an operational aspect of the apparatus occurring between the generation of the data and the holding of the data whenever it is determined that the transmitting and receiving unit has entered inside the guiding catheter.

12. The method according to claim 11, wherein when it is determined that the transmitting and receiving unit has entered inside the guiding catheter, the holding of the data in the memory unit is stopped.

13. The method according to claim 11, further comprising injecting flash liquid to a vicinity of the transmitting and receiving unit, and when it is determined that the transmitting and receiving unit has entered inside the guiding catheter, stopping the injection of the flash liquid to the vicinity of the transmitting and receiving unit.

14. The method according to claim 11, wherein when it is determined that the transmitting and receiving unit has entered inside the guiding catheter, stopping the rotating and axial movement of the transmitting and receiving unit.

15. The method according to claim 11, further comprising constructing a two-dimensional image for real time display from the data held in the memory unit, and wherein the determining whether the transmitting and receiving unit has entered inside the guiding catheter comprises extracting an image of the guiding catheter from the two-dimensional image.

* * * * *